United States Patent
Aubert

(10) Patent No.: US 7,613,481 B2
(45) Date of Patent: Nov. 3, 2009

(54) METHOD FOR THE MANAGEMENT OF INFORMATION STORED ON A SMART CARD READABLE BY A MOBILE TELEPHONE

(75) Inventor: Jean-Charles Aubert, Saint-Geniez-d'olt (FR)

(73) Assignee: Celavie (FR)

( * ) Notice: Subject to any disclaimer, the term of this patent is extended or adjusted under 35 U.S.C. 154(b) by 68 days.

(21) Appl. No.: 10/939,629

(22) Filed: Sep. 13, 2004

(65) Prior Publication Data

US 2005/0037737 A1 Feb. 17, 2005

Related U.S. Application Data

(63) Continuation of application No. PCT/FR03/00811, filed on Mar. 13, 2003.

(30) Foreign Application Priority Data

Mar. 14, 2002 (FR) .................................. 02 03178

(51) Int. Cl.
*H04M 3/00* (2006.01)
*H04M 1/00* (2006.01)
*H04B 1/38* (2006.01)

(52) U.S. Cl. .................... 455/558; 455/414.1; 455/419; 455/559

(58) Field of Classification Search ................. 455/558, 455/411, 412.1, 556, 419, 414.1, 559; 705/3; 707/10
See application file for complete search history.

(56) References Cited

U.S. PATENT DOCUMENTS

| 5,832,488 | A |  | 11/1998 | Eberhardt |  |
| 5,924,045 | A | * | 7/1999 | Thauvin et al. | 455/558 |
| 6,026,007 | A |  | 2/2000 | Jigour et al. |  |
| 6,199,158 | B1 | * | 3/2001 | Hirsch | 713/1 |
| 6,650,892 | B1 | * | 11/2003 | Thiriet | 455/419 |
| 6,665,531 | B1 | * | 12/2003 | Soderbacka et al. | 340/7.21 |
| 2002/0016923 | A1 | * | 2/2002 | Knaus et al. | 713/200 |
| 2003/0013487 | A1 | * | 1/2003 | Joo | 455/558 |
| 2004/0152961 | A1 | * | 8/2004 | Carlson et al. | 600/301 |
| 2004/0235523 | A1 | * | 11/2004 | Schrire et al. | 455/558 |
| 2005/0207562 | A1 | * | 9/2005 | Nachef et al. | 379/357.01 |

FOREIGN PATENT DOCUMENTS

| FR | 2 776 448 |   | 9/1999 |
| FR | 2776448 | * | 9/1999 |
| FR | 2 779 850 |   | 12/1999 |
| WO | 96/08755 |   | 3/1996 |
| WO | 98/15910 |   | 4/1998 |
| WO | 01/97686 |   | 12/2001 |

OTHER PUBLICATIONS http://web.archive.org/web/20011105142255/http://home.kabel foon.nl/~michelj/testcard.htm (see attached).*

(Continued)

*Primary Examiner*—George Eng
*Assistant Examiner*—Brandon J Miller
(74) *Attorney, Agent, or Firm*—DLA Piper LLP (US)

(57) ABSTRACT

A method of managing information from a telecommunication equipment unit comprising a screen and equipped with a SIM memory card connector comprising recording the information in a memory register of a standard SIM card, and exchanging information between the telecommunication equipment unit and the SIM card according to a standardized protocol, without subscriber authentication and connection to a telecommunication network, and wherein a SIM Toolkit application developed in the SIM card is executed, thereby enabling management of the information.

17 Claims, 2 Drawing Sheets

OTHER PUBLICATIONS

Motorola Test Card, Nov. 5, 2001, TestCard Article , printout pp. 1-2 http://web.archive.org/web/20011105142255/http://home:.kabel foon.nl/~michelj/testcard.htm.*

Motorola Test Card, Nov. 5, 2001, TestCard, Article, printout pp. 1-2 http://web.archive.org/web/20011105142255k/http://home:.kabel foon.nl/~michelj/testcard.htm.*

* cited by examiner

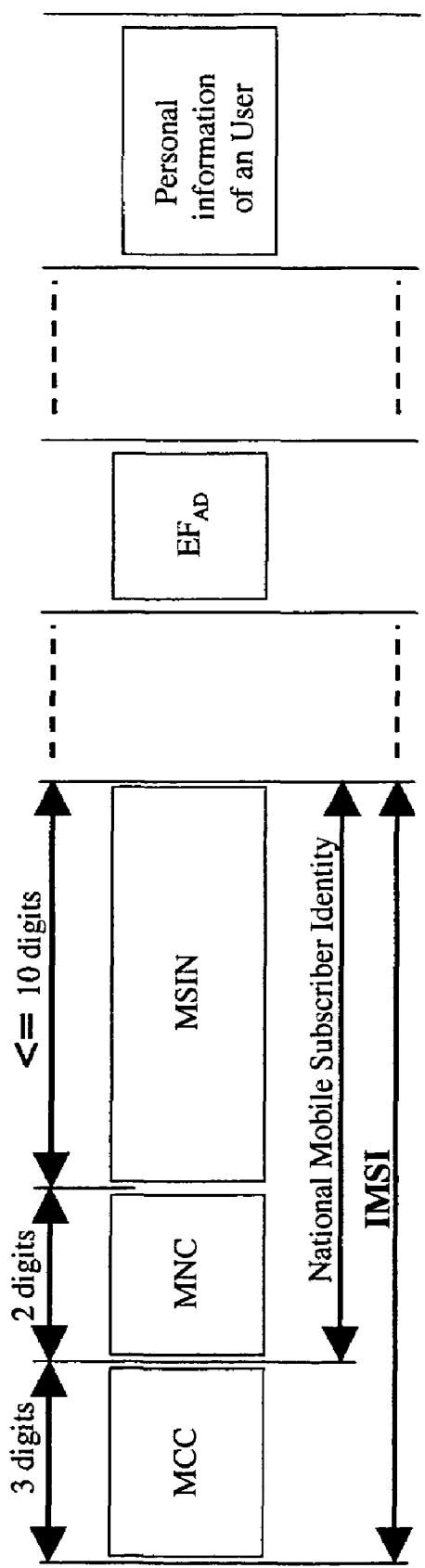
Figure 2 : Composition of the SIM Card

US 7,613,481 B2

METHOD FOR THE MANAGEMENT OF INFORMATION STORED ON A SMART CARD READABLE BY A MOBILE TELEPHONE

RELATED APPLICATION

This is a continuation of International Application No. PCT/FR03/00811, with an international filing date of Mar. 13, 2003 (WO 2003/077163, published Sep. 18, 2003), which is based on French Patent Application No. 02/03178, filed Mar. 14, 2002.

FIELD OF THE INVENTION

This invention pertains to the field of information management, i.e., the acquisition of information by a computer-based system and restoration of the information to the user.

BACKGROUND

Already known in the prior art from U.S. Pat. No. 6,026,007 is an insertable and removable high-capacity digital memory device. Each device from a family of removable digital media devices can be inserted in a host to enable the host to store therein data or an extract from the data. The form factors of the digital media devices in the family and the connector systems used for the digital media devices are compact to minimize the volume of space occupied in the portable device and for easy storage. Several modes of implementation propose an elongated compact form factor which provides an ease and stability of grasping for insertion and withdrawal. The digital media devices of the family have the same cases and are preferably constituted of a rigid or semi-rigid material. The digital media devices of the family preferably uses memory in series which requires little power and line signals such that few electric contracts are necessary. In particular, a small number of durable contact blocks form the contact matrices on the digital media devices, which in conjunction with corresponding contact blocks mounted on an adapted piece enables easy and practical insertion and withdrawal as well as a robust and reliable electrical contact during a long duration of insertion life. The digital memory devices of the family preferably contain a flash memory which enables operating at low voltage, a low consumption of electricity and a safeguarding of the nonvolatile data and at high capacity. The digital media devices of the family are preferably manufactured using surface mounting techniques, particularly the reduced cost "chip on board" technique. The digital media devices interface with the host directly or by means of adaptors. Access is processed by a dedicated controller or another logical element residing in the adaptor or on the host, or by a software program executed on the host.

It describes high-capacity cards and does not pertain to the use of small-memory cards such as the SIM (Subscriber Identification Module) cards intended for subscriber identification by a GSM mobile telephony operator.

Also known in the prior art from WO 98/15910 is a global electronic medical record (GEMR). That invention pertains to systems and methods suitable for a secure, confidential global electronic medical record, managed by the subscriber and which can be updated. These systems and methods, which are used on a network, pertain to the medical information of the connected subscriber, with access to the information, thanks to the network address and a password, being limited solely to the subscriber or an authorized user. Those systems and methods are particularly suitable for medical treatments concerning subscribers traveling abroad, the systems comprising an emblem giving the network address of the global electronic medical record of the subscriber or global electronic medical record servers. The password is communicated by the subscriber to the authorized user who needs to have access to the subscriber's global electronic medical record. According to the preferred implementation, only the subscriber's medical information residing on the global electronic medical records server can be obtained, while according to a more preferential implementation, access to institutional servers or servers of other medical sites makes it possible to obtain a complement of medical information pertaining to the subscriber, the medical information to be incorporated in the subscriber's global electronic medical record. According to the most preferential implementation, the global electronic medical record, which resides on the Web, has hypertext links between the parts of the subscriber's global electronic medical record.

It pertains to electronic medical records and does not pertain to the possibility of managing information by means of an SIM type smart card.

Also known in the prior art from U.S. Pat. No. 5,832,488 is a computer system and a method for programming said system to:

store individual medical data on a storage support, preferably of the size of a credit card;
  add new medical data regarding the individual on the storage support;
  communicate with other computers in order to retrieve the greatest amount of data regarding the individual; and
  enable a second computer to collect and sort the data regarding the individual and other individuals according to certain medical criteria.

That invention provides a solution for the storage of personal data, medical data in this instance, on a central system that can be consulted from a computer connected to said central system. That system, however, is not effective if the information is required in an environment not equipped with a computer, e.g., in the street.

SUMMARY OF THE INVENTION

This invention relates to a method of managing information from a telecommunication equipment unit including a screen and equipped with a SIM memory card connector including recording the information in a memory register of a standard SIM card, and exchanging information between the telecommunication equipment unit and the SIM card according to a standardized protocol, without subscriber authentication and connection to a telecommunication network, and wherein a SIM Toolkit application developed in the SIM card is executed, thereby enabling management of the information.

BRIEF DESCRIPTION OF THE DRAWINGS

Better understanding of the invention will be obtained from the description presented below, on a purely explanatory basis, of one mode of implementation of the invention with reference to the attached figures:

FIG. 2 represents the composition of the IMSI (International Mobile Subscriber Identity).

DETAILED DESCRIPTION

Figure 1:
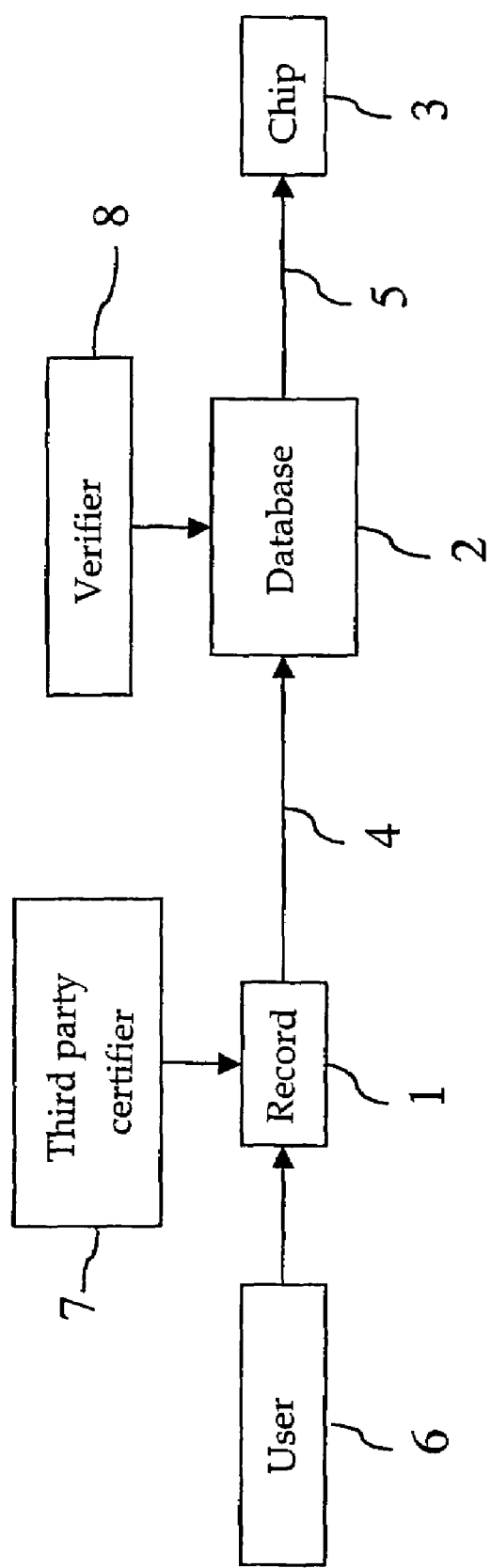
FIG. 1 illustrates the data acquisition process on the chip.

It will be appreciated that the following description is intended to refer to specific embodiments of the invention selected for illustration in the drawings and is not intended to define or limit the invention, other than in the appended claim.

The invention resolves the drawbacks of the prior art by storing the data on a support which can be read by a large number of terminals. The data are thus stored on an SIM smart card which can be read by a mobile telephone. This solution resolves the problem of rapid accessibility to the information because the mobile telephone is a widely distributed, standardized product.

For this purpose, the present invention pertains in its most general sense to a method for information management from a telecommunication equipment unit comprising a screen and equipped with an SIM memory card connector, the method comprising a step of recording the information in the memory registers of a standard SIM card, and a step of exchanging information between the telecommunication equipment unit and the SIM card according to a standardized protocol, characterized in that the step of subscriber authentication and connection to the telecommunication network is avoided, and in that the SIM Toolkit application developed in the SIM card is executed thereby enabling management of the information.

The step of recording the information preferably comprises an operation of recording in the register corresponding to the IMSI number a numeric derivation sequence whose value is not assigned to a telecommunications operator nor to a country, the information not corresponding to the telecommunication information and being recorded in the registers usually intended for the recording of the information required for establishing a session with a telecommunication operator, the information exchange step comprising the inhibition of the establishment of a connection session due to the fact of the detection of the derivation sequence and the loading in the random access memory of the telecommunication equipment unit of the information that can be displayed on the screen of the telecommunication equipment unit from the standardized applications of the telecommunication equipment unit.

The derivation sequence is advantageously constituted of the value "001" for the code corresponding to the MCC and "01" for the code corresponding to the MNC (cf. FIG. 2).

The file $EF_{AD}$ is advantageously present in the card and at the value "800,000" (cf. FIG. 2).

The method advantageously comprises a step of writing on a storage means and step of reading on the storage means, the writing step comprising:
- a step of filling out a record by the user with personal information;
- a step of sending the record to an operator connected to a server linked to a database;
- a step of verification of the record by the operator;
- a step of integrating the record in the database;
- a step of writing the record on a storage means;

said reading step comprising:
- a step of connection of the storage means with a telecommunication equipment unit capable of reading and displaying the information contained in the storage medium;
- a step of displaying the information on the screen of the telecommunication equipment unit;
- the storage means being an SIM type smart card, the telecommunication equipment unit comprising a SIM type smart card reader and the connection step comprising the insertion of the smart card into the reader.

The invention pertains as a nonlimitative example to the field of medical information, notably information pertaining to chronic pathologies such as allergies and diabetes. However, this invention is not restricted to this field of application, but can be employed for the management of diverse types of information such as interactive games, information, applications or files to be loaded in the random access memory of the mobile telephone.

Within the framework defined above, the invention pertains to the use of a smart card of the SIM type which is readable by a standard mobile telephone. This smart card contains the information in question and is thus the vector of the acquisition and restoration.

According to a first aspect, the information not corresponding to the telecommunication information is constituted of numeric sequences executable by the application software programs of the telecommunication equipment unit.

According to another aspect, the information not corresponding to the telecommunication information is constituted of alphanumeric sequences that can be displayed by the software programs of the telecommunication equipment unit.

According to another aspect, the information not corresponding to the telecommunication information is constituted of a game executable by the software programs of the telecommunication equipment unit.

According to one particular mode of implementation, the telecommunication equipment unit is a mobile telephone. This mode of implementation is contrary to the teachings of those skilled in the art which provides that the SIM card is intended for exchanges between a cellular telephone, the subscriber card and the telephony operator in the framework, e.g., of the protocol GSM03-48. The card as known in the art contains a subscriber identifier for establishing the connection as well as cryptologic means employed in the exchanges between the operator and the telephone.

The invention goes against this usual teaching and turns away, in a surprising manner, from the dialogue between the cellular telephone and the card inserted in the reader to cause it to fulfill a new function for which it was not conceived as a local peripheral device outside of the network for the management of a medical information card.

The use of the portable telephone as a universal reader is based on the characteristic of ready access to the telephone. The originality of the method is based among other factors on the fact of diverting the telephone from its object by bypassing the phases of authentication and connection to a mobile telephony network, and operating with the SIM-ToolKit application developed on the card for displaying and spooling menus on the telephone.

In particular, it is necessary to circumvent the SIM-lock possibly implemented on the telephone. SIM-lock is the operation that restricts the use of the telephone solely to SIM cards distributed by the operator that supplied the telephone. One way to circumvent the SIM-lock and gain control is to use the telephone's test mode. For most telephone models, the test mode is obtained by replacing in the IMSI the codes identifying the operator, MCC and MNC, respectively by "001" and "01".

These "codes identifying the operator" correspond to the first five digits of the IMSI (International Mobile Subscriber Identity) the composition of which is represented in FIG. 2. The IMSI is stored on the SIM card in an elementary file (EF) $EF_{IMSI}$. Upon initialization of the SIM card (when applying power to the terminal), the terminal selects the dedicated file $EF_{GSM}$ and requests the preferred language. If this EF is not available or if the languages are not supported, the terminal selects a language by default. It then executes the procedure of verification of the CHV1 (password associated with the SIM card).

If the CHV1 verification procedure is executed successfully, the terminal executes the SIM phase request procedure. In the case of a SIM phase 2, the GSM operating mode only commences if the $EF_{IMSI}$ and $EF_{LOCI}$ are validated. As described in the GSM standard 11.11, the GSM operating mode then commences and the terminal executes the following procedures:

request administrative information;
    request SIM service table;
    request IMSI;
    request access control;
    request HPLMN search period;
    request PLMN selector;
    request localization information;
    request encryption key;
    request BCCH information;
    request prohibited PLMN.

When the initialization of the SIM card has been performed successfully, the terminal is ready for a GSM session. In this invention, passage into test mode leads to avoiding the network identification process. This allows the user to circumvent the operator's SIM-lock and take control of the terminal.

According to one particular mode of implementation, the record is filled out by handwriting and the certification step comprises of applying a specific stamp to the handwritten document.

According to another mode of implementation, the step of filling out the record is electronic and the certification step comprises adding an electronic signature to the electronic document.

The writing step advantageously comprises a supplementary step of encrypting the data contained in the chip. On the other hand, the data contained in the chip can be protected by a code.

The data contained in the database are advantageously encrypted. On the other hand, the data contained in the database can be protected by a code.

The writing step advantageously comprises a supplementary step of loading libraries on the smart card enabling use of the telephone functions: telephone call, language management, operator management.

According to one particular mode of implementation, the smart card does not contain means enabling the telephone in which it is inserted to connect to a communication network.

Before continuing, several definitions for selected terms are set forth below.

The term "third party certifier" corresponds to a person endowed with a means for certifying the information furnished by the user, the means being recognized and approved by the system implementing the invention.

The term "record" corresponds to any support for inputting personal information. In paper form, a record may be constituted of a form on which the user provides information in fields as a function of the headings. In electronic form, a record may be an electronic file containing the fields filled out by the user via an interface. The record may optionally be divided into two parts: the first part is filled out by the user and the second part is filled out by the third party certifier as a function of the knowledge that he has of the user. For example, in the case of medical data, the user provides the information regarding civil status and the third party certifier provides the information regarding diseases, treatments, allergies and emergency referrals for the physician treating the bearer.

The term "user profile" corresponds to the translation of the record into the format of the database. This profile contains the same information as the record, but in a format compatible with the database.

The acquisition method according to the invention comprises the following steps:

a step of filling out the record (1) by the user (6);
    a step of completion of the record (1) by a third party certifier (7): in the particular case of medical data, this certifier is a physician who fills out the fields concerning diseases, treatments, allergies and referral to the user's treating physician;
    a step of certification of the record (1): in the case of a handwritten record, a stamp is applied to the record by the third party certifier and in the case of an electronic record the electronic signature of the third part certifier is applied to the record;
    a step of sending the record (1) to the server containing the database (2) of the user profiles via the link (4);
    a step of verification of the conformity and integrity of the record (1) by a verifier (8), the verifier being either a person or a program;
    an optional step of conversion of the record (1) into the format of the database (2): in the case of a handwritten record, a person transcribes into the format of the database the information contained in the record; in the case of an electronic record, a program is in charge of making the record information correspond to the information required for the constitution of the entry in the database;
    a step of writing the user profile on the SIM chip (3) via the link (5) with a possible conversion of the user profile into a format that can be read and displayed by a standard mobile telephone.

The restoration process comprises the following steps:

a step of insertion of the chip into the telephone's smart card reader;
    a step of reading the information on the chip;
    a step of displaying the information on the screen of the mobile telephone;
    a step of consultation of the information displayed by a person who can be the user or a third party.

According to a particular mode of implementation of the invention, the information contained by the chip is protected by a PIN type code or encrypted such that the reading of this information is contingent on the knowledge of a key (access code or encryption key).

In the same manner, access to the database is restricted by a code or the data contained in the database are encrypted to guarantee the security of the data contained in the database.

Moreover, the chip can contain information enabling use of certain telephone functions other than display: a payment means to enable telephone communication with a preregistered number in the chip, a communication means with the telephone to detect the language in which the telephone is adjusted and display the information in that language.

The invention was described above as an example. It is understood that one skilled in the art can implement different aspects of the invention without going beyond the scope of the appended claims.

The invention claimed is:

1. A method for information management from a primary telecommunication equipment unit, the primary telecommunication equipment unit comprising a screen and equipped with a Subscriber Identity Module (SIM) memory card connector, wherein a SIM Toolkit application developed in a SIM memory card is executed, thereby enabling management of information, the method for information management comprising:

an acquisition phase of information for a database and the SIM memory card, comprising the steps of:

(a) filling out a record by a user with personal information;
(b) sending the record to an operator connected to a server linked to the database;
(c) verifying of the record by the operator;
(d) integrating the record in the database;
(e) writing the record on the SIM memory card in a format useable by a standard telephone, via a link between the database and the SIM memory card, in memory registers of the SIM memory card intended for storing data required for establishing a session with a telecommunication operator;

and a restoration phase of information, comprising the steps of:
(a) inserting the SIM memory card in the connector of the telecommunication equipment,
(b) exchanging information between the telecommunication equipment unit and the SIM memory card according to a standardized protocol, and
(c) inhibiting the means of subscriber authentication and connection to a telecommunication network, the inhibiting step comprising detecting, by the telecommunication equipment unit, a numeric derivation sequence whose value is not assigned to a telecommunication operator or to a country, the numeric derivation sequence being recorded in a memory register of the SIM memory card where an International Mobile Subscriber Identifier (IMSI) number would normally be recorded to bypass a restriction of use of the telecommunication equipment unit to the telecommunication operator that supplied the telecommunication equipment unit, said inhibiting step causing the telecommunication equipment unit to operate as a local peripheral device outside of the network, by bypassing authentication and connection phases to the network, for displaying of the information written in the SIM memory card, the displaying comprising:
(i) loading in a random access memory of the telecommunication equipment unit of information desired to be managed; and
(ii) displaying said information on the screen of the telecommunication equipment unit via standardized applications of the telecommunication equipment unit.

2. The method according to claim 1, wherein the derivation sequence comprises the values "001" for a Mobile Country Code and "01" for a Mobile Network Code.

3. The method according to claim 1, wherein the SIM memory card further comprising an elementary file (EF$_{AD}$) at the value "800,000."

4. The method for information management according to claim 1, comprising a reading step on the SIM memory card, said reading step comprising:

connecting said SIM memory card with a telecommunication equipment unit capable of reading and displaying information contained in said SIM memory card; and
displaying said information on the screen of said telecommunication equipment unit;
the telecommunication equipment unit comprising a SIM memory card reader and the connecting step including insertion of said smart card into said reader.

5. The method according to claim 1, further comprising recording in a memory register of the SIM memory card numeric sequences executable by application software programs of the telecommunication equipment unit.

6. The method according to claim 1, further comprising recording in a memory register of the SIM memory card alphanumeric sequences that can be displayed by one or more software programs of the telecommunication equipment unit.

7. The method according to claim 1, further comprising recording in a memory register of the SIM memory card a game executable by the software programs of the telecommunication equipment.

8. The method according to claim 1, wherein the telecommunication equipment unit is a mobile phone.

9. The method according to claim 1, wherein writing comprises an additional step positioned after filling out the record comprising completing the record by a third party certifier for information requiring the expertise of a third party.

10. The method according to claim 1, wherein filling out the record is handwritten and a certification comprises applying a specific stamp on a handwritten document.

11. The method according to claim 1, wherein filling out the record is electronic and a certification adding an electronic signature to an electronic document.

12. The method according to claim 1, wherein the writing comprises a supplementary step of encrypting at least some data contained in a chip.

13. The method according to claim 12, wherein at least some data contained in the chip are protected by an access code.

14. The method according to claim 1, wherein at least some data contained in the database are encrypted.

15. The method according to claim 1, wherein at least some data contained in the database are protected by at least one access code.

16. The method according to claim 1, wherein writing comprises a supplementary step of loading libraries on the smart card enabling use of the telephone functions selected from a group consisting of placing a call, management of languages, and management of the operators.

17. The method according to claim 1, wherein the SIM memory card lacks a means of enabling access to a telecommunication network by a telecommunication equipment unit in which the SIM memory card is inserted.

* * * * *